(12) United States Patent
Järventie

(10) Patent No.: US 7,582,467 B2
(45) Date of Patent: *Sep. 1, 2009

(54) METHOD AND APPARATUS FOR PROCESSING ORGANIC MATERIAL

(75) Inventor: Jussi Järventie, Kuhmoinen (FI)

(73) Assignee: Preseco Oy, Espoo (FI)

( * ) Notice: Subject to any disclaimer, the term of this patent is extended or adjusted under 35 U.S.C. 154(b) by 354 days.

This patent is subject to a terminal disclaimer.

(21) Appl. No.: 10/573,644

(22) PCT Filed: Nov. 10, 2004

(86) PCT No.: PCT/FI2004/000667

§ 371 (c)(1),
(2), (4) Date: Mar. 28, 2006

(87) PCT Pub. No.: WO2005/044743

PCT Pub. Date: May 19, 2005

(65) Prior Publication Data

US 2007/0105205 A1    May 10, 2007

(30) Foreign Application Priority Data

Nov. 11, 2003    (FI) ................... 20031641

(51) Int. Cl.
*B09B 3/00* (2006.01)
*B09C 1/10* (2006.01)
*C02F 3/34* (2006.01)
*C12M 1/00* (2006.01)
*C12M 3/00* (2006.01)
*C12P 1/00* (2006.01)
*C12S 3/00* (2006.01)
*C02F 3/28* (2006.01)
*C02F 11/04* (2006.01)

(52) U.S. Cl. ............... 435/267; 71/10; 71/15; 71/21; 210/603; 210/612; 210/613; 210/631; 210/903; 210/908; 210/252; 210/259; 423/234; 435/41; 435/262.5; 435/283.1; 435/289.1

(58) Field of Classification Search .............. None
See application file for complete search history.

(56) References Cited

U.S. PATENT DOCUMENTS 7,160,456 B2 * 1/2007 Jarventie ............... 210/603

FOREIGN PATENT DOCUMENTS

| EP | 0486466 A1 | 5/1992 |
|---|---|---|
| EP | 0589155 A1 | 3/1994 |
| EP | 0818424 A2 | 1/1998 |
| GB | 2179057 A | 2/1987 |
| JP | 2071899 A | 3/1990 |
| JP | 2000185300 A | 7/2000 |
| WO | WO 03 097560 A1 | 11/2003 |

OTHER PUBLICATIONS

Database WPI, Week 1985, Derwent Publications Ltd., London, GB; An 1985-046015 & JP 59105895 A (Daido Tokushuko KK), Jun. 19, 1984—abstract.
Patent Abstracts of Japan, vol. 008, No. 222, Oct. 9, 1984 & JP 59105895 A (Kogyo Gijutsuin et al), Jun. 19, 1984—abstract.
Database WPI, Week 1987, Derwent Publications Ltd., London, GB; & JP 62197382 A (Kubota Ltd), Sep. 1, 1987—abstract.
English Translation of Japanese Office Action, Application No. JP 2006-538876, mailed Apr. 14, 2009.

* cited by examiner

*Primary Examiner*—David M. Naff
*Assistant Examiner*—Deborah K. Ware
(74) *Attorney, Agent, or Firm*—Sughrue Mion, PLLC

(57) ABSTRACT

A method and an apparatus for processing organic material, the method employing at least two reactors and including the steps of combining carbon dioxide or carbon-dioxide containing gas and ammonia or ammonia-containing material in a first reactor to form a buffer compound/buffer compounds, then feeding the buffer compound or buffer compounds formed in the first reactor into a second reactor, and performing bioconversion on organic material in the second reactor. In that case, the carbon dioxide of the mixed carbon dioxide gas reacts with the ammonia, forming a buffer compound, such as ammonium bicarbonate and/or ammonium carbonate.

21 Claims, 4 Drawing Sheets

METHOD AND APPARATUS FOR PROCESSING ORGANIC MATERIAL

BACKGROUND OF THE INVENTION

The invention relates to a method for processing organic material and in particular to a method where carbon dioxide or a carbon dioxide-containing gas mixture and ammonia or ammonia-containing material are combined to form buffer compounds, and to an apparatus for implementing the method.

U.S. Pat. No. 4,824,571 discloses a method and an apparatus for degradation of various organic products and wastes in an anaerobic medium. The method generates degraded products and biogas. In the method, the mass to be degraded is introduced into a fermentation vat and the produced biogas is recovered. After this, the biogas is fed back into the vat from the bottom so as to provide a fluidization effect.

U.S. Pat. No. 4,302,236 discloses the use of a composting system for scrubbing gas effluvia. The method comprises removing inorganic acid-forming constituents from a gas stream high in sulphur, in particular. Inorganic groups form inorganic acids in the presence of oxygen or water. The gas stream to be cleaned is guided through active composting biodegradable organic waste, which is held under thermophilic bacteria-phase digestion conditions.

WO publication 93/06 064 discloses a method for neutralizing and recovering gases formed in connection with wet composting. The object of the invention described in the publication is to render harmful, toxic and/or polluting manure gases harmless. According to the publication, part of the gases is recycled to the composed mass so as to improve its nutrient value.

DE publication 3,134,980 discloses a method for mixing biomass in oxygen-free environment in a biogas reactor by means of biogas produced by bacterial strains and stored in biogas storage. In the method, the biogas is mixed with periodic biogas blows. The necessary biogas pressure is provided by means of the bacterial strains in the biogas reactor. The reactor is externally closed and it communicates with the biogas pressure vessel. Pressure is released in the biogas pressure vessel and next it is blown into the biomass, from which the biogas is further conducted into a biogas container.

EP application 486,466 discloses a method for controlled and continuous aerobic biological decomposition of organic wastes. Decomposing material, which is optionally inoculated with a mixture of bacteria and microbes, is fed into the material in the microbiological waste and the degraded material is removed, whereby an oxygen-containing gas is passed in for the degradation. The object of the method described in the publication is to control the degradation of nitrogen-containing products. In the method, $CO_2$ gas is added to the oxygen-containing gas, depending on the $NH_3$ content and the pH of the degradation product, whereby the gas is mixed with a fraction containing no or very little nitrogen. The method described in the publication is an aerobic method.

Organic material is received from various sources from products of plant and animal origins. One problem with organic material degradation plants is that availability of material to be processed is season-dependent and the plant must be able to process even large amounts of organic solids within a short period because they do not allow long storage. Preservation of organic material poses several problems; for instance, preservation produces $NH_3$, which is a toxic compound and prevents microbes from functioning. Currently the bioconversion reactors allow introduction of only low solid contents because $NH_3$ prevents the microbial function in the reactors. Preservation of seasonally produced organic material also causes problems because it cannot be preserved in acidic or basic conditions if conventional bioconversion processes are employed since they are sensitive to variations in the pH. Conventional bioconversion processes are also extremely sensitive to changes in temperature.

A biogas combustion plant is often arranged in connection with a bioconversion plant for combustion of biogas produced in the bioconversion process. The exhaust gas produced in the biogas combustion has a high carbon dioxide content. However, carbon dioxide is a harmful compound to the environment and there is a general objective to get rid of it.

BRIEF DESCRIPTION OF THE INVENTION

The object of the invention is to provide a method and an apparatus implementing the method so as to solve the above-mentioned problems. The object of the invention is achieved by a method and a system which are characterized by what is disclosed in the independent claims. The preferred embodiments of the invention are disclosed in the dependent claims.

The invention is based on combining carbon dioxide or carbon dioxide-containing gas and ammonia or ammonia-containing material in a pressurized reactor, where a buffer compound or buffer compounds are formed. The carbon dioxide or the carbon dioxide in the mixed carbon dioxide gas reacts with the ammonia in the reactor, forming ammonium bicarbonate and/or ammonium carbonate. The formed compound/compounds does/do not inhibit the microbes in the process to the same extent as free ammonia because the formed buffer compound prevents variations in the pH that are adverse to the microbes. The buffer compound or buffer compounds produced in the first reactor are led into a second reactor, which starts a bioconversion process, i.e. anaerobic digestion, in the second reactor or speeds up an ongoing bioconversion process.

The organic material to be processed can be of plant or animal origin. In this context, the organic material refers to any organic substance.

The ammonia may be ammonia gas or an aqueous ammonia solution. The ammonia-containing material may be any material that contains ammonia. The ammonia and/or the ammonia-containing material may originate, for example, either from the biowaste to be processed alone or from a commercial source, if necessary. In particular, organic materials rich in proteins and/or fats produce naturally large amounts of ammonia. The ammonia added to the organic material to be processed or free ammonia produced therein by microbes softens cell membranes so that bioconversion, i.e. hydrolysis, per se also accelerates considerably. The method and apparatus according to the invention can be utilized both in pressurized and unpressurized bioconversion processes.

The carbon dioxide or mixed carbon dioxide-containing gas may originate from a commercial source or from a process where carbon dioxide is produced as the major product or as a by-product. For example, the carbon dioxide may originate from a biogas combustion plant or from biogas produced in bioconversion.

An advantage of the present invention is that organic material can be preserved in basic or acidic conditions before bioconversion. This is particularly advantageous when seasonally produced waste is to be digested. Preservation with an acid or a base can be finally utilized in connection with a bioconversion process. Previously this has not been possible because material preserved with an acid or a base cannot have been digested further. Preservation with an acid or a base also refers to the fact that the organic material can be hygienized before it is brought to bioconversion. In this context, hygienization refers to killing the pathogenic bacteria in the material. Previously hygienization was carried out by heat treatment, i.e. pasteurization, for instance. Thus the system of the present invention provides an alternative to hygienization by heat treatment.

An advantage of the method and system according to the invention is that larger amounts of solid matter can be introduced into the bioconversion. In addition, microbiologically active waste can be stored in an optimal state in view of methane yield so that the hygienic level complies with the EU directives without thermal manipulation. An advantage of the method according to the invention is that a buffer compound/buffer compounds or material containing a buffer compound/buffer compounds can be fed into hydrolysis reactors which have interrupted their process due to excessive ammonia content or in which the hydrolysis process has not started due to excessive ammonia content, and they can be started or their operation can be accelerated. In addition, the method according to the invention enables preservation of organic material longer than before, which facilitates the storage. The ammonia to be formed no longer prevents the processing, but on the contrary, a long storage time pre-processes the waste. The method produces a hydrolysis product and biogas, which are recovered and can be reutilized.

The present invention also provides advantages in view of the operation of the entire bioconversion plant. In the method according to the invention, it is possible to utilize the exhaust gas which is rich in carbon dioxide and produced in biogas combustion and which would otherwise be harmful to the environment. Due to the high carbon dioxide content of the exhaust gas produced in biogas combustion, it can be utilized as a carbon dioxide source in the method according to the invention.

An advantage of the method and apparatus according to the invention is that when the buffer compound/buffer compounds formed in the first reactor are introduced into the second reactor, the bioconversion process stabilizes because variations in the pH decrease. In conventional reactors of hydrolysis processes, the most favourable conditions for the microbes prevail at the bottom of the reactor. In conventional processes, the conditions in the mid-sections of the reactors are reasonably good for the microbes and the conditions in the top layers of the mass in the reactor are poor for the microbes to function. Mixing the hydrolysis mass in the reactor only makes the conditions worse for the microbes in the conventional hydrolysis processes. Instead, the method according to the present invention provides optimal conditions for the microbes to function since the formed buffer compound prevents variations in the pH in the hydrolysis reactor. Thus the stabilization of the process results in improved processing conditions and larger masses of useful microbes in the hydrolysis reactor. Thanks to the larger mass of useful microbes, greater amounts of organic material can be fed into the hydrolysis reactor, or correspondingly, if the same feed quantities are used, the processing time becomes shorter.

Formation of the buffer compound in the first reactor, known as an accelerator or a stabilizer, is a very economical way to improve and speed up the hydrolysis process.

The method and apparatus of the present invention enable particularly effective production of hydrolyzed organic material.

BRIEF DESCRIPTION OF THE FIGURES

The invention will be described in greater detail in connection with preferred embodiments with reference to FIG. 1 in the attached drawings, which is a schematic view of an embodiment of the invention.

DETAILED DESCRIPTION OF THE INVENTION

Figure 1:
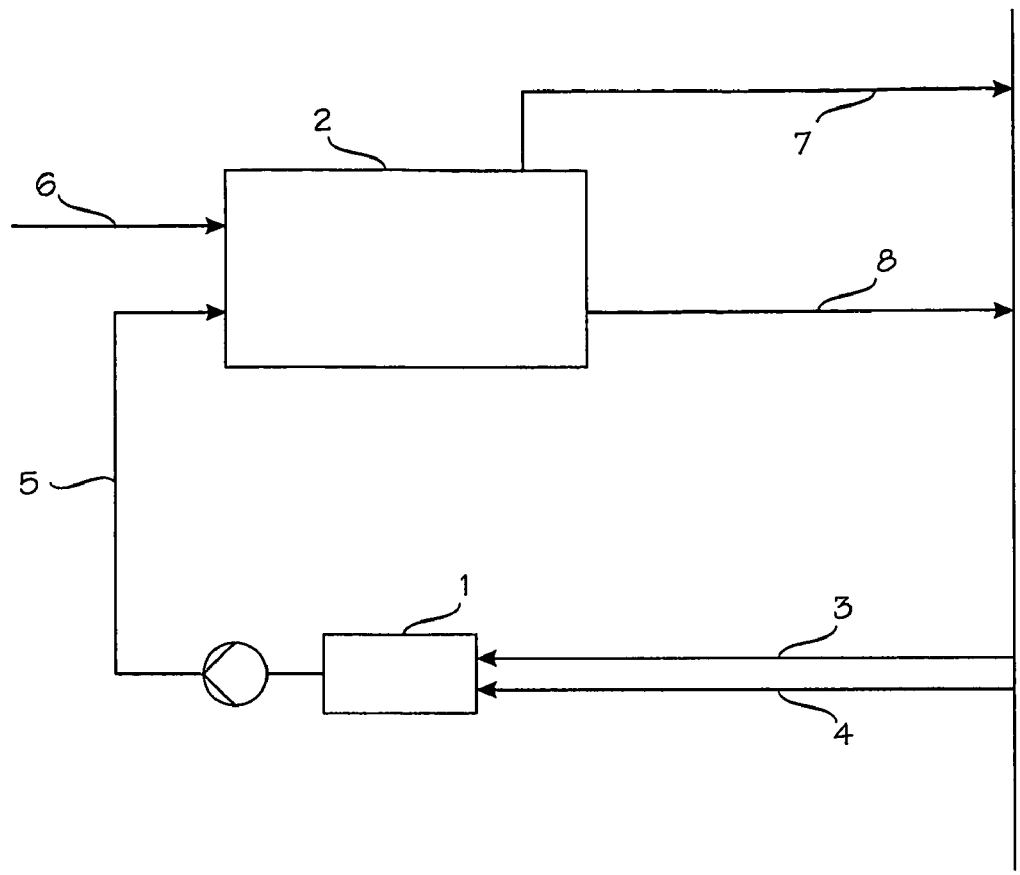
FIG. 1 illustrates an apparatus for implementing a preferred embodiment of the invention.

The invention relates to a method for processing organic material, the method employing at least two reactors and comprising the steps of
a) combining carbon dioxide or carbon-dioxide containing gas and ammonia or ammonia-containing material in a first reactor to form a buffer compound/buffer compounds,
b) feeding the buffer compound or buffer compounds formed in the first reactor into a second reactor, and
c) performing bioconversion on organic material in the second reactor.

Here the first reactor refers to a reactor or reactors into which carbon dioxide or carbon dioxide-containing gas and ammonia and/or ammonia-containing material are fed. This reactor can be considered as a kind of accelerator which starts a bioconversion process or speeds up a bioconversion process that has already started in another reactor.

The carbon dioxide-containing gas mixture preferably contains 1 to 100% of carbon dioxide, more preferably 20 to 100%.

The ammonia-containing material preferably contains 0.1 to 100% of ammonia, more preferably 0.5 to 100%. The ammonia-containing material may be, for example, ammonia-containing wastewater, organic material rich in ammonia or any other ammonia-containing material.

Here the second reactor refers to any reactor or reactors that process bioconversion. There may be several bioconversion processing reactors.

Reactors may be any reaction vessels or containers, or they can be mere pipe sections. A person skilled in the art is able to design suitable reactors to meet the needs of each particular installation.

In this context, bioconversion refers to hydrolysis which is performed partly or completely on organic material. The bioconversion can be a pressurized or an unpressurized process.

Organic material is fed into a bioconversion process reactor. The pressure in the process reactor is above the atmospheric pressure or the normal atmospheric pressure. As the organic material decomposes, biogas containing $CH_4$ and $CO_2$ is produced.

The reactor or reactors where the buffer compound or buffer compounds are produced are pressurized. The pressure is preferably at least approximately 1.8 bar.

In the first reactor, there is thus formed a buffer compound which is fed into the second reactor, in which case additions of acid or base in the second reactor do not cause considerable changes in the pH and the conditions are optimal for the microbes to function. The buffer compounds produced may be any compounds with a buffering property.

The method according to the present invention is particularly advantageous for starting a bioconversion process or for accelerating an ongoing bioconversion process. In the literature, there are several references to the toxicity of ammonia.

Previously, an ammonia content of 3000 mg/l was regarded as toxic and an ammonia content of 1500 to 3000 mg/l as inhibiting. Now, it has been surprisingly found, however, that the ammonia content of the material to be treated may be considerably higher and bioconversion takes place nevertheless.

The method according to the present invention is particularly advantageous when organic material is processed at a biogas combustion plant or in its immediate vicinity. Bioconversion produces hydrolyzed material and biogas. The produced biogas is converted into electric energy by burning it at a biogas combustion plant. The exhaust gas produced by biogas combustion is rich in carbon dioxide and thus harmful to the environment. This exhaust gas can be utilized as a carbon dioxide source in the method according to the present invention. In that case, there is no need to provide a biogas combustion plant with a separate gas cleaning plant.

The pressurized first reactor produces ammonium bicarbonate, for example, because two gases, ammonia and carbon dioxide (disassociated to $NH_4^+$ and $HCO_3^-$ ions), tend to achieve as small a space as possible. In that case, a reactant ammonium ion binds to a carbonic acid ion to produce ammonium bicarbonate or ammonium carbonate, depending on the amount of free ammonia in the reaction solution. Both of these salts act as buffers with the free ammonia as well as the carbonic acid at a ratio of 1:10. Since the living conditions of anaerobic microbes depend to a great extent on the amount of free ammonia and the pH, i.e. as the pH rises, the vital functions of the microbes become weaker, the presence of a buffer is extremely advantageous, particularly in feeds having a high dry matter content and materials that have already produced ammonia anaerobically. Also, carboxyl acids, such as acetic acid, propionic acid or valerianic acid, formed in the bioconversion or existing in the organic material, form a buffer with the free ammonia. Pressure contributes to the formation of buffers.

The organic matter to be processed by the method of the invention can be preserved in acidic or basic conditions prior to being fed into the reactor. This means that the material to be introduced into bioconversion is hygienized prior to the bioconversion.

The bioconversion to be performed in the method according to the present invention may be mesophilic or thermophilic. In this context, the term mesophilic denotes that the bioconversion is performed at a temperature below 40° C. In this context, the term thermophilic denotes that the bioconversion is performed at a temperature of 40 to 70° C., preferably 55 to 65° C. The conventional thermophilic conversion has typically been difficult to manage but the method of the invention allows easy implementation of the thermophilic bioconversion.

For instance, the method of the invention enables that storage and transport conditions of fish obtained by biomanipulation do not cause extra costs as regards preservability, temperature, storage time, etc.

It is advantageous to supply the produced buffer compound/buffer compounds from the bottom of the bioconversion reactor through the reaction mixture to carry out mechanical mixing.

The organic material is material of animal origin, such as fish or fish waste, fowl or fowl waste, material of plant origin, such as cereal, cultivated plant or cultivated plant waste, e.g. barley, cabbage, potato or potato peel. The organic material can also be material of microbial origin, such as yeast or yeast waste, e.g. genetically manipulated yeast waste. The organic material can further be a mixture of the above-mentioned materials. In addition, the organic material can be any kind of wastewater that contains organic substances.

The bioconversion can be carried out at a pressure above the atmospheric pressure, for example at a pressure of approximately 1.2 to 6 bar, preferably at a pressure of 2 to 4 bar. The bioconversion can also be carried out at a normal atmospheric pressure. Preferably, the bioconversion is pressurized.

The bioconversion is carried out by means of micro-organisms present in the organic material and/or by means of added micro-organisms.

The method employs at least two reactors, one of which is used for forming a buffer compound/buffer compounds and the other for bioconversion. The method according to the invention is preferably implemented as continuous circulation.

The ammonia employed in the method is preferably produced in the hydrolysis of the organic material. Buffer compound/buffer compounds formed in the first reactor are added to the second reactor where the bioconversion takes place. It is also possible to optionally add organic, partly hydrolyzed material to the bioconversion reactor.

The buffer compound or buffer compounds resultant from the ammonia and carbon dioxide reaction contain ammonium bicarbonate and/or ammonium carbonate and free ammonia and/or carbonic acid. The ratio between the ammonium bicarbonate or ammonium carbonate and free ammonia and/or carbonic acid is 1:10.

The hydrolyzed product obtained from the organic material can be recovered and utilized as a soil conditioner, fertilizer or a fertilizer-like product or as a repellent, for instance.

The biogas produced in the bioconversion product is preferably recovered and can be used as a greenhouse gas, for heating, for producing electricity or as a fuel, for instance. The cleaned biogas contains carbon dioxide less than 25%, usually 15 to 20%.

The invention also relates to an apparatus for processing organic material. An example of the apparatus according to the invention is illustrated in FIG. 1. The apparatus for processing organic material comprises at least one first reactor 1, at least one second reactor 2, a pipe 3 for feeding carbon dioxide or carbon dioxide-containing gas into the first reactor 1, a pipe 4 for feeding ammonia or $NH_3$-containing material to reactor 1, a pipe 5 for transferring the buffer compound to the second reactor 2, a pipe 6 for transferring organic material to reactor 2, a pipe 7 for transferring biogas from reactor 2 and a pipe 8 for transferring hydrolyzed or partly hydrolyzed material from reactor 2.

Here the first reactor refers to a reactor or reactors into which carbon dioxide or carbon dioxide-containing gas and ammonia and/or ammonia-containing material are fed. This reactor can be considered as a kind of accelerator which speeds up the bioconversion process in the first reactor.

Here the second reactor refers to a reactor or reactors that process bioconversion. The reactor or reactors may be pressurized or at a normal atmospheric pressure.

In the following, the operation of the apparatus according to the invention will be described in greater detail. Carbon dioxide or carbon dioxide-containing gas is fed into a first reactor 1 via pipe 3 and ammonia or ammonia-containing material via pipe 4, after which a buffer compound or buffer compounds are produced in the reactor. The first reactor 1 is pressurized. The pressure in the first reactor is preferably approximately 1 to 10 bar, more preferably 2 to 6 bar. The buffer compound or buffer compounds produced in the first reactor 1 are transferred via pipe 5 to a second reactor 2. Organic material is transferred or has already been transferred to the second reactor 2 via pipe 6. The transfer of the buffer compound to the second reactor 2 starts the bioconversion process or, if the bioconversion process is underway, the transfer of the buffer compound or buffer compounds to reactor 2 accelerates the bioconversion process underway in the reactor. Biogas generated by the bioconversion process is removed from the second reactor 2 via pipe 7, and a hydrolyzed or a partly hydrolyzed product is removed via pipe 8. The second reactor 2 may be pressurized or at normal pressure.

It is obvious to a person skilled in the art that as technology advances, the inventive concept can be implemented in various ways. The invention and its embodiments are thus not restricted to the above examples but they may vary within the scope of the claims.

EXAMPLES

The following gas bottles were used in the tests:

| | |
|---|---|
| Methane $CH_4$ | 99.5% |
| Carbon dioxide $CO_2$ | 100% |
| Ammonia $NH_3$ | 0.5% |
| Nitrogen $N_2$ | 100% |

Gas yield and measuring equipment:

The contents used were obtained from the gas bottles by means of a gas diluter (Environics Inc.).

The contents of gases departing from the pressure vessel were measured by a FTIR gas analyzer (GASME™).

The test vessel was a pressure vessel of about 30 l, where the pressure was kept at about 4 bar during the gas feed.

Tests carried out:

The vessel contained about 25 l water, to which ammonium hydroxide was added, if necessary, to obtain the required ammonia content. Gas mixtures were fed into this solution with pressure.

The incoming total flow was kept at 5 l/min.

Tests in the ammonia solution:

Test 1

Nitrogen was first fed into water having an ammonia content of 2000 mg/l, whereby ammonia was released in gas form. After the content had stabilized, the following gas mixture was fed:

| | |
|---|---|
| $CH_4$ | 60% |
| $CO_2$ | 30% |
| $N_2$ | 10% |

Figure 2:
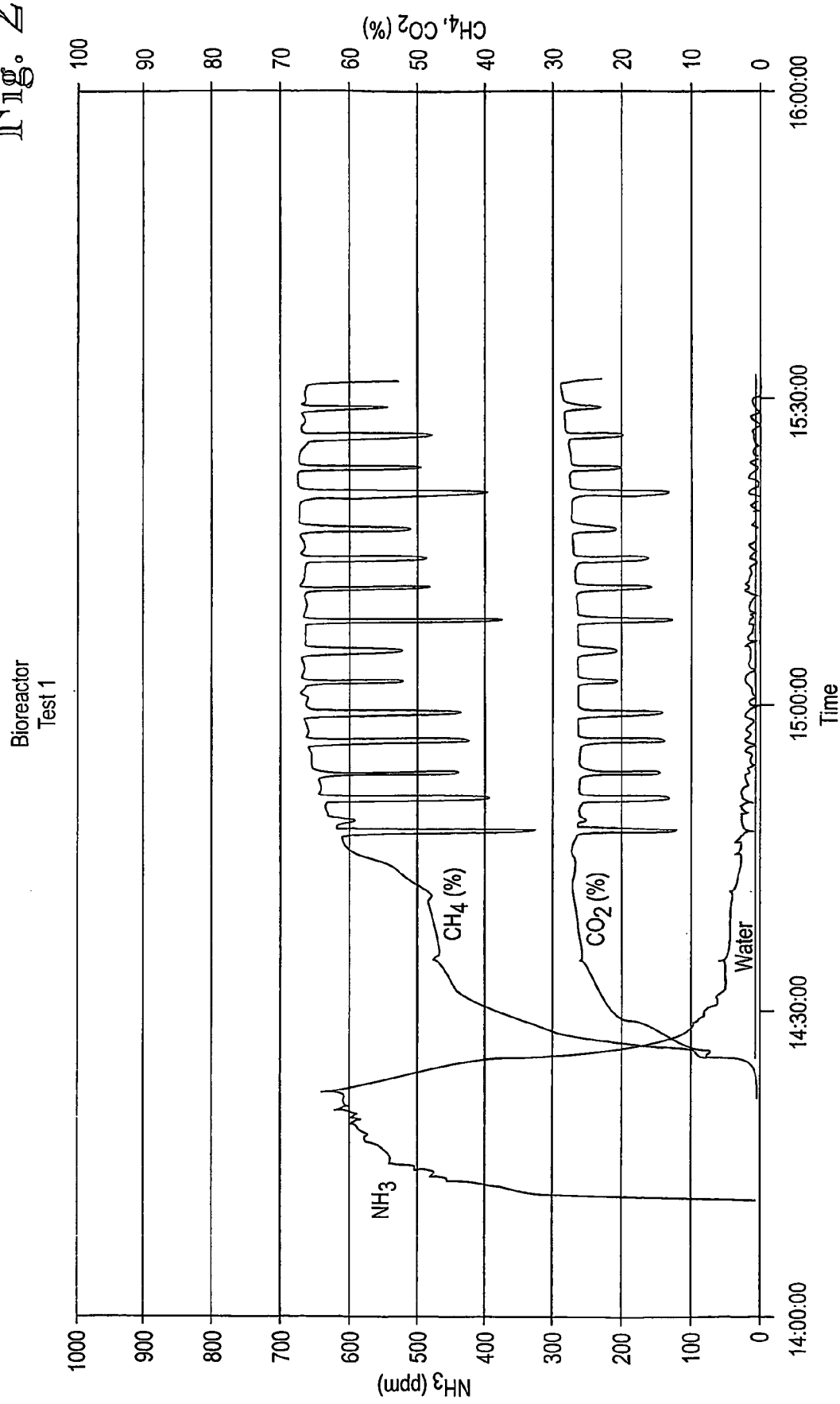
FIG. 2 illustrates the results of test 1 graphically.

The results of test 1 are presented graphically in FIG. 2. Table 1 below shows the development of the pH value and the amount of ammonium bicarbonate as the test proceeded.

TABLE 1

| Sample # | Time (min) | pH | $NH_4HCO_3$(mg/l) |
|---|---|---|---|
| 1 | 3 | 9.55 | 3400 |
| 2 | 6.5 | 9.45 | |
| 3 | 9 | 9.36 | |
| 4 | 12 | 9.27 | 3800 |
| 5 | 15 | 9.16 | |
| 6 | 18 | 9.08 | |
| 7 | 21 | 8.97 | |
| 8 | 24 | 8.84 | |
| 9 | 27 | 8.74 | 9400 |
| 10 | 30 | 8.6 | |

TABLE 1-continued

| Sample # | Time (min) | pH | $NH_4HCO_3$(mg/l) |
|---|---|---|---|
| 11 | 33 | 8.41 | |
| 12 | 36 | 8.17 | |
| 13 | 39 | 7.98 | 12000 |
| 14 | 42 | 7.78 | |
| 15 | 45 | 7.63 | 12000 |

Test 2

Nitrogen was first fed into water having an ammonia content of 2000 mg/l whereby ammonia was released in gas form. After the content had stabilized, the following gas mixture was fed:

| | |
|---|---|
| $CH_4$ | 60% |
| $N_2$ | 40% | and after the outgoing contents had stabilized, the following gas mixture was fed:

| | |
|---|---|
| $CH_4$ | 60% |
| $CO_2$ | 20% |
| $N_2$ | 20% |

Figure 3:
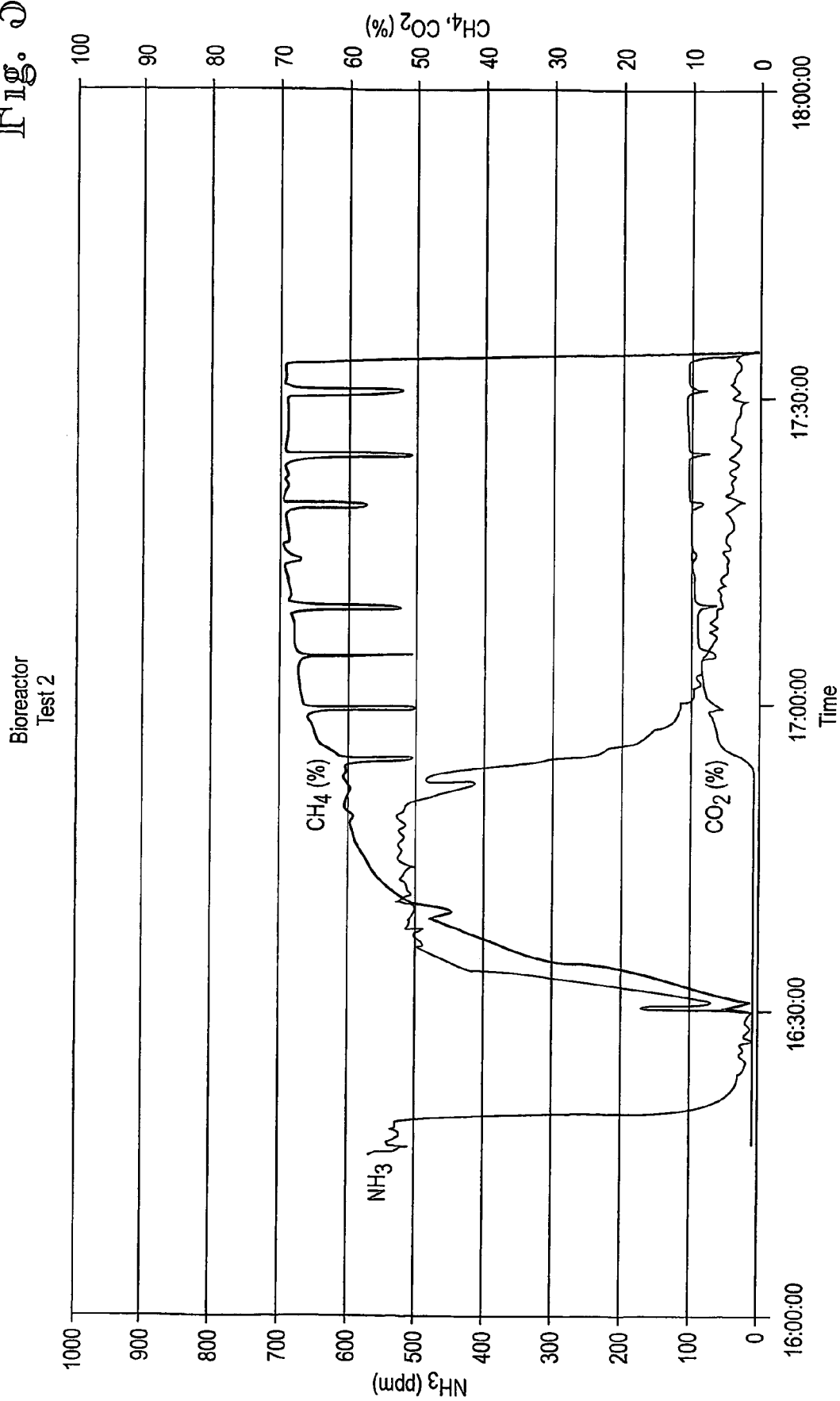
FIG. 3 illustrates the results of test 2 graphically.

The results of test 2 are presented graphically in FIG. 3. Table 2 below shows the development of the pH value and the amount of ammonium bicarbonate as the test proceeded.

TABLE 2

| Sample# | Time (min) | pH | $NH_4HCO_3$(mg/l) |
|---|---|---|---|
| 1 | 0 | 11.24 | 2100 |
| 2 | 10 | 11.24 | |
| 3 | 20 | 11.24 | |
| 4 | 25 | 11 | 2700 |
| 5 | 30 | 10.5 | 3800 |
| 6 | 35 | 10.22 | |
| 7 | 40 | 10.04 | 4700 |
| 8 | 45 | 9.89 | |
| 9 | 50 | 9.74 | |
| 10 | 55 | 9.64 | |
| 11 | 60 | 9.5 | 7300 |

Test 3

Test 3 was carried out using ammonia gas. The following gas mixture was fed into pure water in a vessel:

| | |
|---|---|
| $CH_4$ | 60% |
| $N_2$ | 40% | and after the outgoing contents has stabilized, the following gas mixture was fed:

| | |
|---|---|
| $CH_4$ | 60% |
| $CO_2$ | 20% |
| $N_2$ | 20% |

After this, the following gas mixture was fed into the water:

| | |
|---|---|
| $CH_4$ | 70% |
| $CO_2$ | 28% |
| $N_2$ | 12% |

After the above-mentioned gas flushing, the following gas mixture was fed into the water:

| | |
|---|---|
| $NH_3$ | 0.5% |
| $N_2$ | 99.5% |

Figure 4:
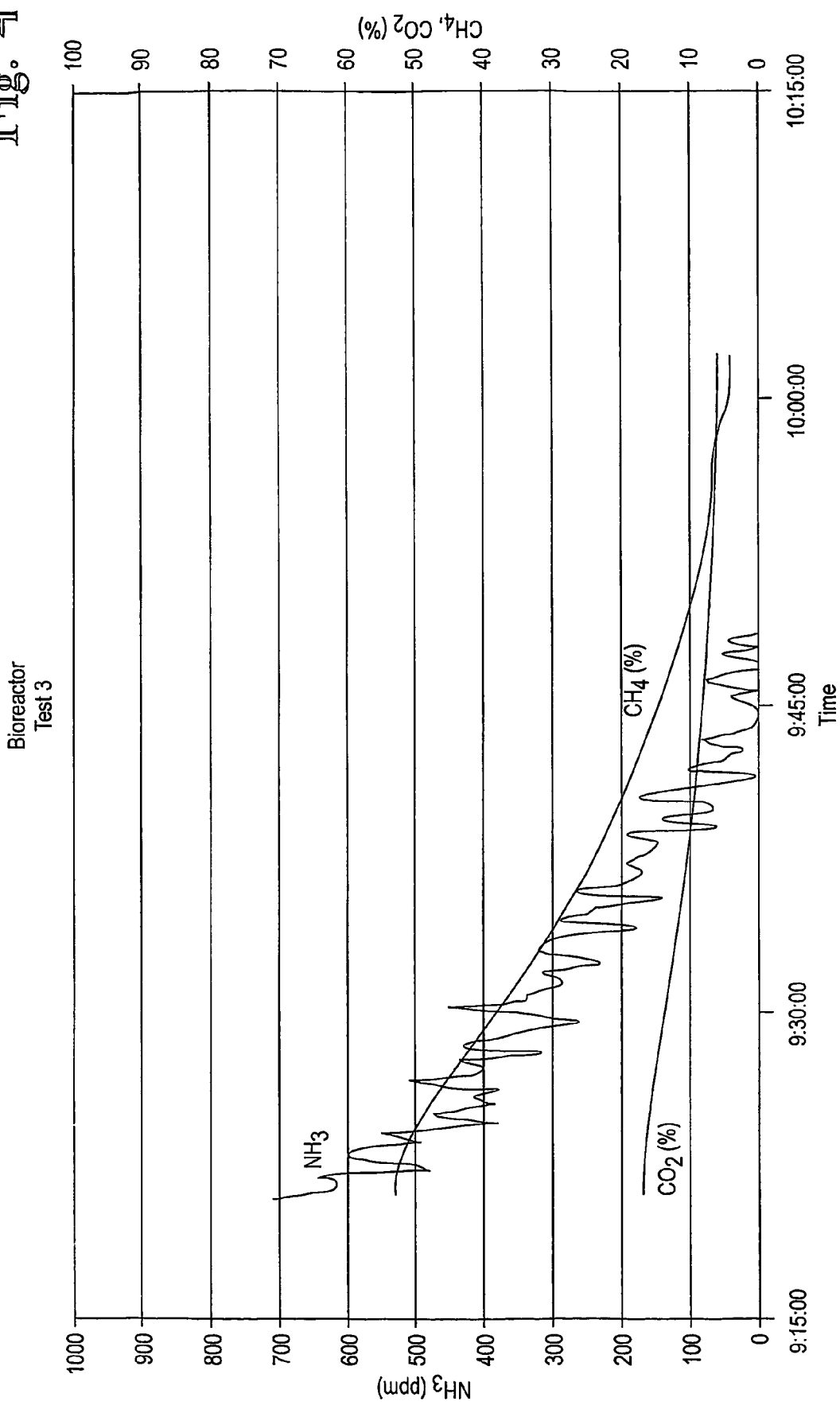
FIG. 4 illustrated the results of test 3 graphically.

The results of test 3 are presented graphically in FIG. 4.

Test 4

100-% $CO_2$ gas was fed into a 10-liter container including 0.2-% $NH_4$ solution. The feeding rate was 1 l/min. The pressure was increased starting from 2 bar to 8 bar and the formed $CO_3^-$ content was measured. Table 3 illustrates the effect of pressure on the formation of a buffer compound/buffer compounds.

TABLE 3

| Time (min) | Pressure (kPa) | pH | $CO_3$ (mg/l) |
|---|---|---|---|
| 8 | 2 | 9.47 | 8500 |
| 21 | 3 | 9.16 | 12800 |
| 25 | 4 | 8.9 | 14100 |
| 28 | 5 | 8.55 | 17100 |
| 37 | 6 | 8.11 | 17900 |
| 42 | 7 | 7.15 | 25700 |
| 60 | 7.8 | 6.87 | 26000 |

Test 5

100-% $CO_2$ gas was fed into a 30-liter container including 0.2-% $NH_4$ solution. The feeding rate was 3 l/min. The pressure was increased starting from 2 bar to 8 bar and the formed $CO_3^-$ content was measured. Table 4 illustrates the effect of pressure on the formation of a buffer compound/buffer compounds.

TABLE 4

| Time (min) | Pressure (kPa) | pH | $CO_3$ (mg/l) |
|---|---|---|---|
| 5 | 3 | 9.35 | 9400 |
| 13 | 4 | 8.93 | 15400 |
| 18 | 5 | 8.5 | 20500 |
| 25 | 6 | 7.6 | 22200 |
| 30 | 7 | 7.28 | 26100 |
| 37 | ~8 | 7.11 | 26000 |

The invention claimed is:

1. A method for bioconversion of organic material, which employs at least two reactors and comprises the steps of
   a) combining carbon dioxide or carbon-dioxide containing gas and ammonia or ammonia-containing material in a first, pressurized reactor to form a buffer compound/buffer compounds,
   b) feeding the buffer compound or buffer compounds formed in the at least one first reactor into at least one second reactor, and
   c) performing bioconversion on organic material in the at least one second reactor to produce biogas and hydrolyzed or partly hydrolyzed organic material.

2. A method according to claim 1, in which the organic material is material of animal origin.

3. A method according to claim 2, in which the organic material is fish or fish waste, fowl or fowl waste.

4. A method according to claim 1, in which the organic material is material of plant origin.

5. A method according to claim 4, in which the organic material is selected from the group consisting of cabbage, potato and potato peel.

6. A method according to claim 1, in which the organic material is yeast or yeast waste.

7. A method according to claim 1, in which the carbon dioxide-containing gas contains 1 to 100% of carbon dioxide.

8. A method according to claim 7, in which the carbon dioxide-containing gas contains 20 to 100% carbon dioxide.

9. A method according to claim 1, in which the ammonia-containing material contains 0.1 to 100% of ammonia.

10. A method according to claim 9, in which the ammonia-containing material contains 0.5 to 100% ammonia.

11. A method according to claim 1, in that in which the ammonia-containing material is ammonia-containing wastewater.

12. A method according to claim 1, in which the bioconversion is carried out at pressure which is above the atmospheric pressure.

13. A method according to claim 12, in which the bioconversion is carried out at a pressure of about 1.2 to 6 bar.

14. A method according to claim 13, in which the bioconversion is carried out at a pressure of about 2 to 6 bar.

15. A method according to claim 1, in which the bioconversion is unpressurized.

16. A method according to claim 1, in which the pressure in the first reactor is over 1.8 bar.

17. A method according to claim 1, in which the bioconversion is carried out under anaerobic conditions.

18. A method according to claim 1, in which the ammonia used is produced by hydrolysis of the organic material.

19. A method according to claim 1, in which the buffer compounds produced contain ammonium bicarbonate or ammonium carbonate and free ammonia and/or carbonic acid.

20. A method according to claim 19, in which the buffer compounds produced contain ammonium bicarbonate or ammonium carbonate and free ammonia and/or carbonic acid at a ratio of 1:10.

21. An apparatus for bioconversion of organic material, which comprises at least one first pressurized reactor configured to combine carbon dioxide or carbon dioxide-containing gas and ammonia or ammonia-containing material to form a buffer compound/buffer compounds,
   a pipe configured to feed carbon dioxide or carbon dioxide-containing gas into the at least one first pressurized reactor,
   a pipe configured to feed ammonia or ammonia-containing material into the least one first pressurized reactor,
   at least one second reactor configured to perform bioconversion,
   a pipe configured to transfer the buffer compound/compounds from the at least one first pressurized reactor to the at least one second reactor,
   a pipe configured to transfer organic material to the at least one second reactor,
   a pipe configured to transfer biogas from the at least one second reactor, and
   a pipe configured to transfer hydrolyzed or partly hydrolyzed organic material from the at least one second reactor.

* * * * *